United States Patent [19]

Lattanzi et al.

[11] Patent Number: 5,310,727

[45] Date of Patent: May 10, 1994

[54] PHARMACEUTICAL COMPOSITIONS FOR PARENTERAL USE CONTAINING A CALCITONIN AS THE ACTIVE INGREDIENT

[75] Inventors: Filippo Lattanzi; Riccardo Vanni, both of Siena, Italy

[73] Assignee: Scalvo S.p.A., Siena, Italy

[21] Appl. No.: 620,399

[22] Filed: Nov. 30, 1990

Related U.S. Application Data

[63] Continuation of Ser. No. 61,664, Jun. 15, 1987, abandoned.

[30] Foreign Application Priority Data

Jun. 20, 1986 [IT] Italy ................. 20865 A/86

[51] Int. Cl.⁵ ............................................. A61K 37/30
[52] U.S. Cl. ........................................ 514/12; 514/808; 514/2; 530/307; 530/317; 930/60; 930/DIG. 671; 930/DIG. 672; 930/DIG. 670
[58] Field of Search ............... 514/12, 13, 808, 16, 514/2; 424/85.9; 530/307, 317; 930/60, DIG. 670, DIG. 671, DIG. 672

[56] References Cited

U.S. PATENT DOCUMENTS

| | | | |
|---|---|---|---|
| Re. 32,347 | 3/1987 | Neher et al. | 530/307 |
| 4,241,051 | 12/1980 | Christie et al. | 530/307 |
| 4,338,335 | 7/1982 | McAleer et al. | 424/89 |
| 4,514,331 | 4/1985 | Kaiser et al. | 530/307 |
| 4,613,500 | 9/1986 | Suzuki et al. | 514/13 |
| 4,659,696 | 4/1987 | Hirai et al. | 514/16 |

FOREIGN PATENT DOCUMENTS 0156242 10/1985 European Pat. Off. .......... 424/89

OTHER PUBLICATIONS

British Pharmacopoeia 1980, vol. II, pp. A13-6-A137,662 (Dec. 1, 1980).
Chemical Abstracts, vol. 102, No. 24, Jun. 17, 1985, p. 342, col. 2, abstr. No. 225984y.
Chemical Abstracts, vol. 76, No. 13, Mar. 27, 1972, p. 280, col. 2, abstr. No. 84114v.
Chemical Abstracts, vol. 103, No. 25, Dec. 23, 1985, p. 371, col. 1, abstr. No. 209192d.
Bell et al, Journal of the American Chemical Society, 1968, pp. 2704-2706.

*Primary Examiner*—Merrell C. Cashion, Jr.
*Assistant Examiner*—T. D. Wessendorf
*Attorney, Agent, or Firm*—Birch, Stewart, Kolasch & Birch

[57] ABSTRACT

A freeze-dried pharmaceutical composition for parenteral administration which includes a therapeutically effective amount of a calcitonin, as the active ingredient, and human albumin.

The injectable solution which is obtained by dissolving the freeze-dried composition in a physiologically acceptable solvent is also described.

14 Claims, No Drawings

PHARMACEUTICAL COMPOSITIONS FOR PARENTERAL USE CONTAINING A CALCITONIN AS THE ACTIVE INGREDIENT

This application is a continuation of application Ser. No. 07/061,664, filed on Jun. 15, 1987, now abandoned.

The present invention refers to a new, freeze-dried, pharmaceutical composition suitable for parenteral administration, which comprises a therapeutically effective amount of a calcitonin, as the active ingredient, and human albumin, and to the injectable solution which is obtained by dissolving the freeze-dried product in a suitable, physiologically acceptable, solvent.

Calcitonins are calcium regulating hormones which are secreted from the thyroid gland, in mammals, and from the ultimobranchial gland, in non-mammals. Their chemical structure corresponds to a single poly-peptide chain containing 32 amino acid residues. The amino acid sequence, however, considerably differs among the animal species, particularly showing a marked difference between the mammalian calcitonins (chiefly human calcitonin and porcine calcitorin) and those of non-mammalian origin (mainly salmon calcitonin and eel calcitonin), whereas the latter ones have shown a more potent specific biological activity (IU/mg).

The over-all action of the calcitonins is to oppose the bone and renal effects of parathyroid hormone, thus inhibiting bone resorption and showing a hypocalcemic and hypophosphatemic action. Animal calcitonin administration is therefore used in the therapy of severe hypercalcaemia associated with neoplastic disease, hyperparathyroidism, and vitamin D intoxication. It is also suitable in the treatment of idiopathic hypercalcaemia during infancy, in osteoporosis, and in Sudek's and Paget's diseases. Calcitonin is typically administered parenterally, and mainly, subcutaneously or intramuscularly. There is, however, a problem facing the industrial pharmacy expert, on how to formulate such a product in order to obtain pharmaceutical preparations stable enough to allow industrial scale production, and to ensure correlation of the administered dose to the prescribed therapeutically effective dose, and repeatability of the selected dosages.

For the time being, just to overcome the former of the above two problems, most of the dosage forms on the market, consist of single-dose calcitonin-containing freeze-dried products and solvent ampules used to reconstitute the injectable solutions just prior to their administration (see, for instance, the brand-products Cibacalcin ®, Calcitar ®, Staporos ®, etc.).

The latter problem as indicated above, is of particular interest in the present case because calcitonin is a quite potent drug which is generally administered in very low doses, typically from about 0.001 to about 0.1 mg. Furthermore, calcitonins have a high tendency to be adsorbed on the walls of the container, either be it on glass or plastic (Parson J. A. "Calcitonin : Proceedings of a Symposium on Thyrocalcitonin and C Cells" (1968)) thus creating serious problems concerning the reproducibility of a constant and therapeutically effective dosage.

It is known, in industrial pharmacy, that sometimes it is possible, in the formulation of some hormones which need to be administered in very small doses and have a tendency to be absorbed on the container walls, to reduce said inconvenience by the addition of some proteins, whose effect, if any, and its entity, can not be foreseen, or the mechanism through which they act has not been yet been understood.

It has now been found that suitably formulating a calcitonin, and particularly, salmon or eel calcitonin, with human albumin, it is possible to get freeze-dried products, whose biological titer, evaluated in the injectable solutions obtained therefrom by reconstitution, remains constant for more than three years. This means not only that the product, when formulated according to the present invention, is stable for at least three years but also that it is possible to guarantee the administration of suitably selected doses, thus allowing meaningful therapy and valuable results.

It has also been found that human albumin is compatible with the active ingredient and does not affect its chemico-physical characteristics, absorption pattern and metabolic pathway.

A first object of the present invention is therefore a freeze-dried composition for parenteral administration containing a calcitonin as the active ingredient, characterized in that it contains from about 0.005 to about 2.5 mg of human albumin per IU of calcitonin. According to a preferred embodiment of the present invention said composition will contain from about 0.05 to about 2 mg of human albumin per IU of calcitonin, and, according to a most preferred embodiment, from about 0.1 to about 1.2 mg of human albumin per IU of calcitonin. Albumin which can suitably be employed for said formulation is purified human albumin for human use complying with the standard requirements of the most recent Italian Pharmacopeia (F.U.). More particularly, either freeze-dried human serum albumin ready for use in humans, or the Albumin Injectable Solution, which consists of an aqueous solution containing from 5 to 26% (w/v) albumin, may be utilized.

To prepare a lyophilized formulation according to the present invention, calcitonin and albumin, in suitably selected proportions, are dissolved in Water for Injection up to the desired concentration.

The solution may contain, if desired, further additives or excipients, which must be compatible with the active principle and, if they are not removed during the freeze-drying stage, they must also be compatible with the route of administration. In particular, the literature available as well as the experimental results obtained show that slightly acidic conditions favourably affect the preparation stability (see, for instance, F.U. IX Ed. Vol. II, pages 316 and 1414, where an optimum pH of from 3.5 to 5.5 is reported for the "Injectable Porcine Calcitonin Solution", and a pH comprised between 3.9 and 4.5 is reported for the "Salcatonin" injectable preparation), an additional excipient suitably used in the new formulation of the present invention, is an organic or inorganic acid, acid salt or acid buffer, in a concentration suitable to provide a pH value within the range 3.5-5.5, preferably 4.0-5.0, and, more preferably, 4.4-4.8. Said acid, acid salt or acid buffer must be physiologically acceptable for parenteral administration at the doses employed Monobasic sodium phosphate is the acid salt of choice for said purpose, but other compounds, such as for instance citric acid, may as well be used in said preparations. Additional excipients which might conveniently be employed in the formulations of the present invention are, for instance, carbohydrates such as dextrose, mannitol or dextran, which could be added to the composition just to increase the amount of solids present.

Additives, which also might be used in preparing the calcitonin-containing formulations of the present invention, are local anesthetics and/or antiemetics suitable for parenteral administration.

In actual practice, once a solution is obtained containing the active principle, human albumin, and all the other excipients or additives, if any, in the desired concentrations, said solution is transferred into the previously sterilized individual unit containers, by pouring into each vial a volume of the thus obtained solution which provides the selected amount of active principle per single-dose administration unit.

The filled up vials are then loaded into the freeze-drying chamber and freeze-dried until the product is dry. When the freeze-drying stage is complete, the vials are sealed by closing the opening with a rubber closure, while still in the freeze-drying chamber, under rigorously sterile conditions. Rubber closures are finally held in place by means of aluminum caps which cover the closures and are crimped under the lid of the vials.

As for the concentration of the active principle in the solution, the solution volume which is charged into each vial, and the capacity of the vials (interrelated parameters which can suitably be modified, depending on the desired concentration of active principle in the end dosage unit), these may vary within wide ranges bearing in mind however that preferred single-dose administration units will contain an amount of calcitonin in the range of from 1 to 250 IU, generally corresponding to a content in mg comprised between 0.0002 and 1.25 mg, depending on the titer of the starting material, and also that a suitable vial capacity, according to conventional pharmaceutical practice, is generally comprised between 1 and 5 ml and preferably between 1 and 2.5 ml.

For its use in therapy, the freeze-dried formulation of the present invention is redissolved in a suitable solvent and injected soon after reconstitution. The solvent of choice, in this case, is sterile water for injectable preparations because both calcitonin and albumin are very soluble in water. However, other aqueous solvents which are capable of dissolving the freeze-dried composition, are compatible with the selected administration route and do not negatively interfere with the active principle and the excipients or additives employed, may be used for the preparation of the injectable formulation. A further object of the present invention is therefore an injectable formulation obtained by dissolving the above freeze-dried product in a suitable solvent. A still further object of the present invention is a pharmaceutical single-dose administration unit which consists of a lyophilized composition as discussed above containing from 1 to 250 IU of calcitonin, and from about 1 to about 5 ml of a suitable solvent.

The following examples illustrate in further detail some representative compositions of the present invention and the process for their preparation. It has to be understood that these examples are not to be interpreted as a limitation to the scopes of the invention because, on the basis of the information therein contained, it is possible for the average skilled technician to alter the active principles, concentrations, preparation techniques falling within the above descriptive portion yet different from those specifically exemplified.

EXAMPLE 1

Process for preparing the freeze-dried product

Human albumin (660 g) and mono-basic sodium phosphate monohydrate (136.62 g) are charged in a suitable glass vessel and dissolved, by stirring, in water for injectable preparations, checking, when a homogeneous solution is obtained, the pH of the solution (pH=4.6±0.2).

Eel calcitonin (1.650.000 IU) is then dissolved therein and the solution is brought to the desired volume by the addition of water for injectable preparations still checking the pH of the obtained solution.

The solution is then filtered through a sterilizing Millipore 0.22 $\mu$m filter collecting the filtrate in a sterile glass flask kept in a sterile chamber.

With a suitable liquid filler, the solution is distributed into previously sterilized vials (33.000), which are then loaded into the freeze-drier and lyophilized.

When lyophilization is complete, the vials are sealed while still in the freeze-drier (stoppering). Aluminum caps are then applied to the vials at the end of process line by means of a mechanical crimper.

Each vial will contain a lyophilized product having the following composition:

| | |
|---|---|
| eel calcitonin | 50 IU |
| human albumin | 20 mg |
| monobasic sodium phosphate monohydrate | 4.14 mg |

By following substantially the same procedure as above but using a higher amount of eel calcitonin (3.300.000 IU instead of 1.650.000 IU), 33.000 vials, each containing a lyophilized product with the following composition, are obtained:

| | |
|---|---|
| eel calcitonin | 100 IU |
| human albumin | 20 mg |
| monobasic sodium phosphate monohydrate | 4.14 mg |

For the preparation of the above lyophilized product the following ingredients are employed:

eel calcitonin (synthetic) having the following structural formula:

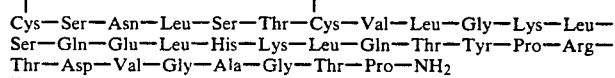

Cys—Ser—Asn—Leu—Ser—Thr—Cys—Val—Leu—Gly—Lys—Leu—
Ser—Gln—Glu—Leu—His—Lys—Leu—Gln—Thr—Tyr—Pro—Arg—
Thr—Asp—Val—Gly—Ala—Gly—Thr—Pro—NH$_2$ as a white fluffy powder, easily soluble in water, which must contain not more than 10 % water and not more than 15 % acetic acid, and, in each mg, not less than 4.000 IU of calcitonin;

human albumin complying with the standard specifications reported in the pertinent monograph of F.U. IX Ed., Vol. II, page 69; and monobasic sodium phosphate monohydrate fulfilling the requirements of the US Pharmacopoeia (USP) XXI Ed., page 976.

EXAMPLE 2

Process for the preparation of the solvent ampules

Recently distilled water for injectable preparations complying with the requirements of the Italian Pharmacopeia (F.U. IX Ed., Vol.II, page 52), is poured into a suitable glass vessel. It is filtered through a sterilizing Millipore ® 0.20 μm membrane filter into previously sterilized glass containers under rigorously sterile conditions. With a suitable liquid filler machine, the filtered solvent is distributed in glass ampules. These are then sterilized in steam autoclave for 40 minutes at 121° C., and sealed.

EXAMPLE 3

Evaluation of the stability of the lyophilized formulation

Stability of the lyophilized products obtained as described in example 1, containing, respectively, 50 or 100 IU of eel calcitonin per dosage unit, has been evaluated by assaying samples of the lyophilized formulations, stored at room temperature, for "visual appearance" and "biological titer".

The results are reported in following Tables I and II:

TABLE I

Stability data of the lyophilized product of Example 1 containing 100 IU/vial, stored at room temperature

| Parameters | Time (mo) | | | |
|---|---|---|---|---|
| | 0 | 12 | 24 | 36 |
| Visual appearance | White porous mass | unaltered | unaltered | unaltered |
| Biological titer (IU) | 89.2 | 96.2 | 109.0 | 109.9 |

TABLE II

Stability data of the lyophilized product of Example 1 containing 50 IU/vial, stored at room temperature

| Parameters | Time (mo) | | | |
|---|---|---|---|---|
| | 0 | 12 | 24 | 36 |
| Visual appearance | White porous mass | unaltered | unaltered | unaltered |
| Biological titer (IU) | 52.75 | 61.4 | 59.95 | 51.8 |

An HPLC quantitative determination of the active principle in the same lyophilized products, stored for three years at room temperature, gave highly satisfactory results.

More particularly, the content of a vial prepared as in Example 1, containing 100 IU of eel calcitonin, stored for three years at room temperature, was dissolved in a 3% aqueous solution of sodium dodecylbisulphate (1 ml) and analysed by HPLC showing a titer of 98.0 IU, corresponding to 98% of the theoretical titer.

The same analysis has been performed also with a sample of the lyophilized product of Example 1 containing 50 IU of eel calcitonin per vial, giving a titer of 47.5 IU, corresponding to 95% of the theory.

We claim:

1. A lyophilized pharmaceutical composition comprising calcitonin and from 0.005 to 2.5 mg of human albumin per IU of calcitonin.

2. The composition of claim 1 wherein the amount of human albumin is between 0.05 and 2 mg per IU of calcitonin.

3. The composition of claim 2 wherein the amount of human albumin is between 0.1 and 1.2 mg per IU of calcitonin.

4. The composition of claim 1 wherein calcitonin is salmon calcitonin or eel calcitonin.

5. The composition of claim 4 wherein calcitonin is eel calcitonin.

6. The composition of claim 1 which further comprises a pharmaceutically acceptable acid, acid salt or acid buffer in a concentration sufficient to impart a pH of from 3.5 and 5.5 to the composition.

7. The composition of claim 6 wherein the concentration of said acid, acid salt or acid buffer is sufficient to impart a pH of from 4.0 and 5.0 to the composition.

8. The composition of claim 7 wherein the concentration of said acid, acid salt or acid buffer is sufficient to impart a pH of from 4.4 and 4.8 to the composition.

9. The composition of claim 6 wherein said acid salt is monobasic sodium phosphate.

10. The composition of claim 1 containing from 1 to 250 IU of calcitonin.

11. A single-dose administration unit consisting of the composition of claim 10 and from 1 to 5 ml of a physiologically acceptable solvent.

12. The single-dose administration unit of claim 11 wherein the amount of calcitonin is between 10 and 200 IU.

13. The single-dose administration unit of claim 11 wherein the physiologically acceptable solvent is sterile water.

14. A lyophilized pharmaceutical composition which comprises eel calcitonin and from 0.1 to 1.2 mg of human albumin.

* * * * *